United States Patent
Leinweber et al.

(10) Patent No.: US 12,138,638 B2
(45) Date of Patent: Nov. 12, 2024

(54) COMPOSITION AND METHOD FOR USE OF 1-ALKYL-5-OXOPYRROLIDINE-3-CARBOXYLIC ACIDS AS COLLECTORS FOR PHOSPHATE AND LITHIUM FLOTATION

(71) Applicant: Clariant International, Ltd., Muttenz (CH)

(72) Inventors: Dirk Leinweber, Kelkheim (DE); Adriana Grossmann, Mühldorf (DE); Wagner Claudio Da Silva, São Paulo (BR); Leandro Seixas Bicalho, Belo Horizonte (BR)

(73) Assignee: Clariant International Ltd, Muttenz (CH)

( * ) Notice: Subject to any disclaimer, the term of this patent is extended or adjusted under 35 U.S.C. 154(b) by 318 days.

(21) Appl. No.: 17/470,795

(22) Filed: Sep. 9, 2021

(65) Prior Publication Data
US 2023/0091787 A1   Mar. 23, 2023

(51) Int. Cl.
| | |
|---|---|
| B03D 1/01 | (2006.01) |
| B03D 1/008 | (2006.01) |
| C02F 1/24 | (2023.01) |
| C07D 207/277 | (2006.01) |
| C02F 103/10 | (2006.01) |

(52) U.S. Cl.
CPC .............. *B03D 1/01* (2013.01); *B03D 1/008* (2013.01); *C02F 1/24* (2013.01); *C07D 207/277* (2013.01); *B03D 2201/02* (2013.01); *C02F 2103/10* (2013.01)

(58) Field of Classification Search
CPC .. C07D 207/277; B03D 2201/02; B03D 1/01; B03D 1/008
See application file for complete search history.

(56) References Cited

U.S. PATENT DOCUMENTS

| | | | | |
|---|---|---|---|---|
| 2,173,909 A * | 9/1939 | Kritchevsky | .......... | B03D 1/008 554/108 |
| 2,757,125 A * | 7/1956 | Mudrak | .................... | C11D 3/28 548/530 |
| 3,224,975 A * | 12/1965 | Hinkamp | ............. | C10M 133/44 508/297 |
| 3,859,208 A | 1/1975 | Knocke | | |
| 4,098,687 A | 7/1978 | Yang | | |
| 4,139,481 A | 2/1979 | Wang | | |
| 4,158,623 A | 6/1979 | Wang | | |
| 4,192,739 A | 3/1980 | Smith, Jr. | | |
| 4,207,178 A | 6/1980 | Smith, Jr. | | |
| 4,298,708 A * | 11/1981 | Schulze | ................ | B03D 1/016 521/902 |
| 4,790,932 A | 12/1988 | Kottwitz | | |
| 6,712,217 B2 * | 3/2004 | Kremer | .................. | B03D 1/008 252/61 |
| 10,478,829 B2 * | 11/2019 | Bhambhani | ............ | B03D 1/008 |
| 11,607,696 B2 * | 3/2023 | Smolko-Schvarzmayr | .................. | B03D 1/01 |
| 2003/0146136 A1 * | 8/2003 | Kremer | .................. | B03D 1/008 209/166 |
| 2012/0088698 A1 | 4/2012 | Kayser | | |
| 2015/0238976 A1 * | 8/2015 | Da Silva | ................ | B03D 1/008 209/4 |

FOREIGN PATENT DOCUMENTS

| | | | | |
|---|---|---|---|---|
| DE | 102009030411 A1 * | 12/2010 | .......... | B01F 17/0042 |
| WO | WO-0187490 A1 * | 11/2001 | ............. | B03D 1/008 |
| WO | WO-2010149251 A1 * | 12/2010 | ............. | B01F 17/0042 |
| WO | WO-2021052939 A1 * | 3/2021 | ............. | B03D 1/016 |
| ZA | 9009347 | 9/1991 | | |

OTHER PUBLICATIONS

Extended European Search Report issued in App. No. EP21199322, dated May 6, 2022, 4 pages.
International Search Report and Written Opinion issued in App. No. PCT/EP2022/069546, dated Oct. 12, 2022, 13 pages.

* cited by examiner

*Primary Examiner* — Clare M Perrin

(57) ABSTRACT

The invention relates to a flotation agent for lithium or phosphate ore, comprising at least one fatty acid and at least one 1-alkyl-5-oxopyrrolidine-3-carboxylic acid or 1-alkenyl-5-oxopyrrolidine-3-carboxylic acid or a mixture thereof of the formula (1)

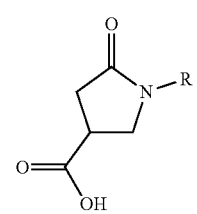

(1)

wherein R is a $C_7$ to $C_{21}$ alkyl or alkenyl group, wherein the amount of fatty acid is from 70 to 99 wt.-%, and wherein the amount of the 1-alkyl-5-oxopyrrolidine-3-carboxylic acid or 1-alkenyl-5-oxopyrrolidine-3-carboxylic acid of the formula (I) is from 1 to 30 wt.-%.

19 Claims, No Drawings

COMPOSITION AND METHOD FOR USE OF 1-ALKYL-5-OXOPYRROLIDINE-3-CARBOXYLIC ACIDS AS COLLECTORS FOR PHOSPHATE AND LITHIUM FLOTATION

This invention relates to the separation of phosphate and lithium minerals by means of flotation from crude ores or preconcentrates using fatty acids as collecting agents and at least one 1-alkyl-5-oxopyrrolidine-3-carboxylic acid or 1-alkenyl-5-oxopyrrolidine-3-carboxylic acid or a mixture thereof as a co-collector.

Phosphate and lithium minerals are found usually together with worthless gangue minerals, for example silicate minerals and carbonate minerals, such as quartz and calcite. The separation of the gangue minerals from phosphate and lithium minerals is performed by flotation. Flotation usually requires a collector to be present.

Collecting agents can be described as organic-chemical compounds which, in addition to one or more non-polar hydrocarbon radicals, carry one or more chemically active polar groups which are capable of being adsorbed on active centers of the mineral and thus rendering the latter hydrophobic.

As is known, flotation or froth flotation is a widely used concentration process for mineral ores, in which one or more valuable minerals are separated from the worthless ones. The preparation of the mineral ore for flotation is carried out by dry, or preferably wet grinding of the precomminuted ore to a suitable particle size. The particle size depends, on the one hand, on the degree of intergrowth, i.e. on the size of the individual particles in a mineral assemblage, and on the other hand also on the maximum particle size which is still possible to be floated and which can differ widely depending on the mineral. The type of flotation machine used also has an influence on the maximum particle size which can be floated.

Further steps in preparing phosphate and lithium ore for flotation can represent a preparation of worthless material on the one hand, for example by a heavy medium separation (separating off relatively coarse constituents), and on the other hand, desliming (separating off ultrafine of the finest particles). The removal of magnetic minerals, which are almost always present for both ore types, by means of magnetic separation is also a possible preconcentrating method. The invention is not limited to flotation processes preceded by a preconcentration step.

With respect to the minerals to be recovered in the froth, two procedures must be distinguished. In direct flotation, the valuable mineral or minerals is or are collected in the froth which is generated on the surface of the flotation suspension, and this requires that their surfaces have previously been rendered hydrophobic by means of one or more collecting agents. The worthless minerals are then present in the flotation tailings. In reverse flotation, the worthless minerals are rendered hydrophobic by collecting agents, while the flotation tailings form the actual valuable concentrate. The present invention relates to the direct flotation of the phosphate and lithium minerals, but it can also follow a preceding reverse flotation step which, for example, represents a flotation of silicate-type minerals by means of cationic collecting agents.

A large number of anionic and amphoteric chemical compounds are known as collecting agents for phosphate minerals, and these include, for example, unsaturated fatty acids (oleic acid, linoleic acid, linolenic acid) and the sodium, potassium or ammonium soaps thereof, monoalkyl and dialkyl phosphates, alkanesulfocarboxylic acids, alkylarylsulfonates, acylaminocarboxylic acids and alkylaminocarboxylic acids. In addition, collecting agents are known which are adducts of sulfosuccinic acid (see, for example U.S. Pat. Nos. 4,207,178, 4,192,739, 4,158,623 and 4,139,481). Many of these classes of chemical compounds, however, suffer from unsatisfactory selectivity which does not allow the production of saleable phosphate concentrations or makes it necessary to use a relatively large quantity of regulating reagents, especially depressants for the gangue minerals.

In the flotation of phosphate ore with fatty acids according to ZA-9009347, it is known that the flotation output can be improved by using, in addition to the collecting agent (a fatty acid), a dispersing agent, such as, for example, a nonyl phenol with 2-5 mol of ethylene oxide (EO) and an aliphatic alkoxylated alcohol with the chain length $C_{11}$-$C_{15}$ which contains 2-4 mol of EO. A further improvement arises if an alcohol with the chain length $C_1$-$C_{15}$ is dissolved in the dispersing agent. This alcohol improves the emulsifiability of the dispersing agent. However, alkoxylated nonyl phenols are regarded as questionable from the standpoint of environmental protection and toxicology. There is a tendency to avoid the use of alkoxylated nonyl phenols in flotation operations and to use a suitable replacement therefore For lithium concentration, it is known that saturated or unsaturated fatty acids are used as collecting agents. U.S. Pat. No. 3,859,208 describes the use of fatty acids derived from tall oil and erucic acid, containing 20 to 22 carbon atoms and a mixture of fatty acids containing from about 15 to about 75% of a fatty acid containing 20 to 22 carbon atoms balance with $C_{18}$ or lower fatty acids. U.S. Pat. No. 4,098,687 also describes the use of saturated or unsaturated fatty acid containing about 18 to 20 carbon atoms, water soluble soaps derived from said fatty acids, and mixtures thereof. Although the fatty acids are widely applied as collecting agents for lithium flotation, these classes of chemical compounds, however, achieved very low or unsatisfactory lithium recovery.

The instant invention is therefore concerned with finding compositions which are useful as collecting agents for phosphate and lithium flotation. Surprisingly, it has now been found that 1-alkyl-5-oxopyrrolidine-3-carboxylic acids or 1-alkenyl-5-oxopyrrolidine-3-carboxylic acid or a mixture thereof may be used as a co-collector together with fatty acids, whereby the $P_2O_5$ and $Li_2O$ recovery is improved with respect to the use of only fatty acids.

One embodiment of the instantly claimed invention provides a flotation agent for phosphate and lithium ore, comprising a collecting agent composition which contains at least one fatty acid and at least one 1-alkyl-5-oxopyrrolidine-3-carboxylic acid or 1-alkenyl-5-oxopyrrolidine-3-carboxylic acid according to Formula 1.

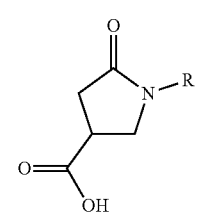

(1)

wherein R is a $C_7$ to $C_{21}$ alkyl or alkenyl group.

The technical effect of the at least one 1-alkyl-5-oxopyrrolidine-3-carboxylic acid or 1-alkenyl-5-oxopyrrolidine-3- carboxylic acid or a mixture thereof present in the flotation agent is that it is a co-collector for phosphate and lithium ores. In the following, the expressions co-collector will relate to the 1-alkyl-5-oxopyrrolidine-3-carboxylic acid or 1-alkenyl-5-oxopyrrolidine-3-carboxylic acid or a mixture thereof. In formula (I), R is preferably a $C_{11}$ to $C_{19}$, more preferably a $C_{13}$ to $C_{18}$ residue. In a further preferred embodiment, R is a $C_{11}$ to $C_{19}$, more preferably a $C_{12}$ to $C_{17}$ alkenyl residue having at least one double bond.

The most preferred embodiment of formula (I) as a co-collector of phosphate ore is wherein R is a $C_{18}$ alkenyl group.

The most preferred embodiment of formula (I) as a co-collector of lithium ore is wherein R is a $C_{12}$ alkyl group.

The technical effect of the fatty acid present in the flotation agent is that it is a collector for phosphate and lithium ores. The fatty acid which makes up the main constituent of the flotation agent according to the invention is preferably a linear or branched monocarboxylic acid having 8 to 26 carbon atoms. For this purpose, the fatty acids known in the prior art as collectors can be used. The amount of fatty acid is 70 to 99, particularly 80 to 95, especially 85 to 90 wt.-% of the total flotation agent weight.

The flotation agent according to the invention comprises between 1 and 30%, particularly 5 to 20%, especially 10 to 15% by weight of the 1-alkyl oxopyrrolidine-3-carboxylic acid or 1-alkenyl-5-oxopyrrolidine-3-carboxylic acid or a mixture thereof of co-collector, based on the total flotation agent weight.

The flotation agent according to the invention is preferably used in amounts from 100 to 1000 g/t of solid ore for the flotation of phosphate ores. The amount of co-collector agent according to the invention added in the case of separate collector dosing is preferably between 100 and 350 g/t, in particular between 150 and 300 g/t of solid ore.

The flotation agent according to the invention can, in addition to said constituents of fatty acid and 1-alkyl-5-oxopyrrolidine-3-carboxylic acid or 1-alkenyl-5-oxopyrrolidine-3-carboxylic acid or a mixture thereof, comprise known depressants or further constituents. Such constituents are, for example, foaming agents and aliphatic polyglycol ethers.

Another aspect of this invention is the use of at least one fatty acid and at least one compound of formula (I) in admixture as flotation agents for phosphate and lithium ores.

Another aspect of this invention is a process for flotating phosphate and lithium ores, the process comprising the step of adding the flotation reagent comprising at least one fatty acid and at least one compound of formula (I) to an aqueous suspension of the ore, and aerating the so obtained mixture.

EXAMPLES

Collecting Agent Formulation Preparation for all Examples

A crude soy oil fatty acid was heated to around 60° C. until all solids are molten and are subsequently homogenized. A 1-alkyl-5-oxopyrrolidine-3-carboxylic acid or 1-alkenyl-5-oxopyrrolidine-3-carboxylic acid or a mixture thereof was heated to around 60° C. until all solids are molten and are subsequently homogenized. 85 g of the molten homogenized crude soy oil fatty acid was transferred to a heated beaker and (under stirring at around 100 rpm) 15 g of the molten homogenized 1-alkyl-5-oxopyrrolidine-3-carboxylic acid or 1-alkenyl-5-oxopyrrolidine-3-carboxylic acid or a mixture thereof was added slowly, and the mixture was homogenized for 30 minutes under heating at 60° C.

Materials Used:

TABLE 1

Description of the Fatty Acid and Co-collectors

| | Reagent 1 | Reagent 2 | Ratio Reagent 1: Reagent 2 |
|---|---|---|---|
| Fatty Acid | Crude soy oil fatty acid (Almad S/A) (comparative) | — | 1:0 |
| Co-collector 1 | Itaconic acid | Octylamine | 1:1 |
| Co-collector 2 | Itaconic acid | Laurylamine | 1:1 |
| Co-collector 3 | Itaconic acid | Oleylamine | 1:1 |
| Co-collector 4 | Itaconic acid | Cocoylamine | 1:1 |
| Co-collector 5 | Itaconic acid | Stearylamine | 1:1 |
| Co-collector 6 | Itaconic acid | Dodecyl dipropylene triamine | 1:1 |
| Co-collector 7 | Itaconic acid | Dodecyl dipropylene triamine | 2:1 |
| Co-collector 8 | Itaconic acid | Tallowamine | 1:1 |

Example 1

Applications-Related Investigations for Phosphate Flotation

Froth flotation experiments were conducted using a Denver laboratory flotation cell. 1.00 kg of ground ore was conditioned by stirring at 1100 rpm with 0.66 liter of water (solids content of the pulp 60 wt-%). A depressant (maize corn caustic starch) and the above described collector was added and conditioning continued for 5 minutes thereafter. The solids content of the pulp was adjusted to 30% by adding water. The pH was adjusted to 9.0 and the mixture was stirred for 1 minute.

The stirring was adjusted to 1400 rpm, the air intake was opened, and the ore was floated for 3 minutes, obtaining the rougher concentrate (froth) and rougher tailing (remaining ore in the cell). The rougher concentrate was returned to the flotation cell and was floated again, without adding collector, for 2 minutes at 1000 rpm, obtaining the cleaner concentrate (phosphate concentrate) and cleaner tailing. The cleaner concentrate and cleaner tailing, besides the rougher tailing (final tailing dried at 105±5° C.), were weighed and analysed to determine their phosphate grade by the XRF method (x-ray fluorescence).

The efficiency of Collecting Agent Formulations based on 1-alkyl-5-oxopyrrolidine-3-carboxylic acid or 1-alkenyl-5-oxopyrrolidine-3-carboxylic acid or a mixture thereof (Collecting Agent Formulations P2 to P17) were compared to the pure Fatty Acid (Collecting Agent Formulation P1). The concentration of fatty acid can be reduced, relative to the comparison product, from 100% to 85% thereby improving the recovery and keeping the $P_2O_5$ in acceptable grade. $P_2O_5$ in acceptable grade means a target of ≥35.8 weight-% $P_2O_5$. In addition, total replacement of fatty acid by Collecting Agent Formulation P12 (oleyl 1-alkyl-5-oxopyrrolidine-3-carboxylic acid) improved the phosphate recovery along with keeping the $P_2O_5$ in acceptable grade (Target ≥35.8 wt.-% $P_2O_5$).

TABLE 2

Composition and flotation results for phosphate ore

| Collecting Agent Formulation | Component 1 | % | Component 2 | % | Dosage (g/t) | Grade P$_2$O$_5$ (wt.-%) | Recovery P$_2$O$_5$ (wt.-%) |
|---|---|---|---|---|---|---|---|
| P1 | Fatty Acid | 100 | — | — | 250 | 39.60 | 48.08 |
| P2 | Fatty Acid | 85 | Co-collector 1 | 15 | 250 | 38.91 | 51.78 |
| P3 | Fatty Acid | 85 | Co-collector 2 | 15 | 250 | 39.00 | 53.55 |
| P4 | Fatty Acid | 85 | Co-collector 3 | 15 | 250 | 39.61 | 65.40 |
| P5 | Fatty Acid | 85 | Co-collector 4 | 15 | 250 | 39.97 | 50.11 |
| P6 | Fatty Acid | 85 | Co-collector 5 | 15 | 250 | 38.95 | 55.68 |
| P7 | Fatty Acid | 85 | Co-collector 6 | 15 | 250 | 38.86 | 1.39 |
| P8 | Fatty Acid | 85 | Co-collector 7 | 15 | 250 | 39.99 | 14.57 |
| P9 | Fatty Acid | 85 | Co-collector 8 | 15 | 250 | 39.90 | 37.41 |
| P10 | Fatty Acid | 0 | Co-collector 1 | 100 | 250 | 17.47 | 2.64 |
| P11 | Fatty Acid | 0 | Co-collector 2 | 100 | 250 | 17.47 | 2.64 |
| P12 | Fatty Acid | 0 | Co-collector 3 | 100 | 250 | 39.06 | 81.28 |
| P13 | Fatty Acid | 0 | Co-collector 4 | 100 | 250 | 30.37 | 3.11 |
| P14 | Fatty Acid | 0 | Co-collector 5 | 100 | 250 | n.a. | n.a. |
| P15 | Fatty Acid | 0 | Co-collector 6 | 100 | 250 | 10.25 | 0.58 |
| P16 | Fatty Acid | 0 | Co-collector 7 | 100 | 250 | 14.73 | 0.61 |
| P17 | Fatty Acid | 0 | Co-collector 8 | 100 | 250 | 15.37 | 0.95 |

*n.a. means that there was no flotation observed

Example 2

Materials used are those listed in Table 1 above.

Applications-related investigations for lithium flotation
Froth flotation experiments were conducted using a Denver laboratory flotation cell. 0.8 kg of ground ore was conditioned by stirring at 1500 rpm with 0.8 liter of water (solids content of the pulp 50 wt-%). Collector was added and conditioning continued for 7 minutes thereafter. The pH was adjusted to 10.0 and the mixture was stirred for 1 minute.

The stirring was adjusted to 1300 rpm, the air intake was opened, and the ore was floated for 7 minutes, obtaining the rougher concentrate (froth) and rougher tailings. The rougher concentrate and rougher tailing are dried at 105±5° C., were weighed and analysed to determine their lithium grade by ICP-OES method.

The efficiency of Collecting Agent Formulations based on 1-alkyl-5-oxopyrrolidine-3-carboxylic acid or 1-alkenyl-5-oxopyrrolidine-3-carboxylic acid or a mixture thereof (Collecting Agent Formulation L2 to L17) were compared to the pure Fatty Acid (Collecting Agent Formulation L1). The concentration of fatty acid can be reduced, relative to the comparison product, from 100% to 85% thereby improving the recovery and keeping the Li$_2$O in acceptable grade. Li$_2$O in acceptable grade means a target of ≥4.0 weight-% Li$_2$O, considering the rougher concentrate.

TABLE 3

Composition and flotation results for lithium ore

| Collector Agent Formulation | Component 1 | % | Component 2 | % | Dosage (g/t) | Grade Li$_2$O (wt.-%) | Recovery Li$_2$O (wt.-%) |
|---|---|---|---|---|---|---|---|
| L1 | Fatty Acid | 100 | — | — | 600 | 4.89 | 51.6 |
| L2 | Fatty Acid | 85 | Co-collector 1 | 15 | 600 | 3.85 | 48.5 |
| L3 | Fatty Acid | 85 | Co-collector 2 | 15 | 600 | 4.76 | 77.4 |
| L4 | Fatty Acid | 85 | Co-collector 3 | 15 | 600 | 5.03 | 58.0 |
| L5 | Fatty Acid | 85 | Co-collector 4 | 15 | 600 | 4.86 | 65.5 |
| L6 | Fatty Acid | 85 | Co-collector 5 | 15 | 600 | 5.11 | 40.6 |
| L7 | Fatty Acid | 85 | Co-collector 6 | 15 | 600 | 2.50 | 25.4 |
| L8 | Fatty Acid | 85 | Co-collector 7 | 15 | 600 | 4.33 | 34.3 |
| L9 | Fatty Acid | 85 | Co-collector 8 | 15 | 600 | 3.66 | 17.1 |
| L10 | Fatty Acid | 0 | Co-collector 1 | 100 | 600 | 1.10 | 8.50 |
| L11 | Fatty Acid | 0 | Co-collector 2 | 100 | 600 | 1.43 | 30.9 |
| L12 | Fatty Acid | 0 | Co-collector 3 | 100 | 600 | 3.05 | 12.6 |
| L13 | Fatty Acid | 0 | Co-collector 4 | 100 | 600 | 1.55 | 10.8 |
| L14 | Fatty Acid | 0 | Co-collector 5 | 100 | 600 | n.a. | n.a. |
| L15 | Fatty Acid | 0 | Co-collector 6 | 100 | 600 | 1.24 | 47.5 |
| L16 | Fatty Acid | 0 | Co-collector 7 | 100 | 600 | 1.35 | 26.0 |
| L17 | Fatty Acid | 0 | Co-collector 8 | 100 | 600 | 1.55 | 5.48 |

*n.a. means that there was no flotation observed

The invention claimed is:
1. A flotation agent for a phosphate or a lithium ore, comprising
  from 70 to 99 wt.-%, based on the total weight of the flotation agent, of at least one fatty acid; and from 1 to 30 wt.-%, based on the total weight of the flotation agent, of at least one 1-alkyl-5-oxopyrrolidine-3-carboxylic acid or 1-alkenyl-5-oxopyrrolidine-3-carboxylic acid according to formula (1)

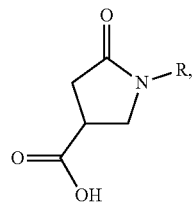

(1)

or a combination thereof, wherein R is a $C_7$ to $C_{21}$ alkyl or alkenyl group.

2. The flotation agent as claimed in claim 1, wherein the fatty acid has from 8 to 26 carbon atoms.

3. The flotation agent as claimed in claim 1, wherein R is a $C_{11}$ to $C_{19}$ alkyl or alkenyl residue.

4. The flotation agent as claimed in claim 1, wherein R is a $C_{13}$ to $C_{18}$ alkyl or alkenyl residue.

5. The flotation agent as claimed in claim 1, wherein R is a $C_{12}$ to $C_{17}$ alkenyl residue having at least one double bond.

6. The flotation agent as claimed in claim 1, wherein the ore is a phosphate ore and R is a $C_{18}$ alkenyl group.

7. The flotation agent as claimed in claim 1, wherein the ore is a lithium ore and R is a $C_{12}$ alkyl group.

8. A process for flotating a phosphate ore, the process comprising the steps of
adding to an aqueous suspension of the phosphate ore, from 100 to 1000 g/t of a flotation agent comprising
from 70 to 99 wt.-%, based on the total weight of the flotation agent, of at least one fatty acid; and
from 1 to 30 wt.-%, based on the total weight of the flotation agent, of at least one 1-alkyl-5-oxopyrrolidine-3-carboxylic acid or 1-alkenyl-5-oxopyrrolidine-3-carboxylic acid according to formula (1)

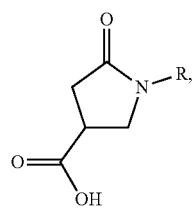

(1)

or a combination thereof, wherein R is a $C_7$ to $C_{21}$ alkyl or alkenyl group,
to produce a mixture; and
aerating the so obtained mixture.

9. The process for flotating a phosphate ore as claimed in claim 8, wherein the fatty acid has from 8 to 26 carbon atoms.

10. The process for flotating a phosphate ore as claimed in claim 8, wherein R is a $C_{11}$ to $C_{19}$ alkyl or alkenyl residue.

11. The process for flotating a phosphate ore as claimed in claim 8, wherein R is a $C_{13}$ to $C_{18}$ alkyl or alkenyl residue.

12. The process for flotating a phosphate ore as claimed in claim 8, wherein R is a $C_{12}$ to $C_{17}$ alkenyl residue having at least one double bond.

13. The process for flotating a phosphate ore as claimed in claim 8, wherein R is a $C_{18}$ alkenyl group.

14. The process for flotating a phosphate ore as claimed in claim 8, wherein R is a $C_{12}$ alkyl group.

15. A process for flotating a lithium ore, the process comprising the steps of
adding to an aqueous suspension of the lithium ore, from 100 to 1000 g/t of a flotation agent comprising
from 70 to 99 wt.-%, based on the total weight of the flotation agent, of at least one fatty acid; and
from 1 to 30 wt.-%, based on the total weight of the flotation agent, of at least one 1-alkyl-5-oxopyrrolidine-3-carboxylic acid or 1-alkenyl-5-oxopyrrolidine-3-carboxylic acid according to formula (1)

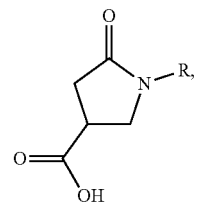

(1)

or a combination thereof, wherein R is a $C_7$ to $C_{21}$ alkyl or alkenyl group,
to produce a mixture; and
aerating the so obtained mixture.

16. The process for flotating a lithium ore as claimed in claim 15, wherein the fatty acid has from 8 to 26 carbon atoms.

17. The process for flotating a lithium ore as claimed in claim 15, wherein R is a $C_{11}$ to $C_{19}$ alkyl or alkenyl residue.

18. The process for flotating a lithium ore as claimed in claim 15, wherein R is a $C_{13}$ to $C_{18}$ alkyl or alkenyl residue.

19. The process for flotating a lithium ore as claimed in claim 15, wherein R is a $C_{12}$ to $C_{17}$ alkenyl residue having at least one double bond.

* * * * *